United States Patent [19]

Schromm et al.

[11] 4,021,485
[45] May 3, 1977

[54] N,N'-BIS-[(β-HYDROXY-β-PHENYL)-ETHYL]-POLYMETHYLENEDIAMINES AND SALTS THEREOF

[75] Inventors: Kurt Schromm; Anton Mentrup; Ernst-Otto Renth, all of Ingelheim am Rhein; Werner Traunecker, Munster-Sarmsheim, all of Germany

[73] Assignee: Boehringer Ingelheim GmbH, Ingelheim am Rhein, Germany

[22] Filed: Nov. 4, 1975

[21] Appl. No.: 628,819

Related U.S. Application Data

[63] Continuation of Ser. No. 246,711, April 24, 1972, abandoned.

[30] Foreign Application Priority Data

Apr. 26, 1971 Austria .................... 3582/71

[52] U.S. Cl. .................... 260/570.6; 260/253; 260/404.5; 260/479 R; 260/501.1; 260/501.18; 260/501.19; 260/501.2; 260/501.21; 260/553 A; 260/556 AR; 260/556.5; 260/556 N; 260/562 P; 260/570.5 C; 424/253; 424/316; 424/330
[51] Int. Cl.² .................... C07C 91/16
[58] Field of Search ..... 260/501.18, 570.6, 570.6 P

[56] References Cited
UNITED STATES PATENTS

| 3,329,709 | 7/1967 | Schmid et al. | 260/570.6 |
| 3,644,353 | 2/1972 | Lunts et al. | 260/247.5 |
| 3,673,187 | 6/1972 | Schromm et al. | 260/253 |

Primary Examiner—Robert V. Hines
Attorney, Agent, or Firm—Hammond & Littell

[57] ABSTRACT

Compounds of the formula $$Ar-CH(OH)-CH_2-NH-\underset{\underset{R_1}{|}}{\overset{\overset{R_1}{|}}{C}}-(CH_2)_m-\underset{\underset{R_1}{|}}{\overset{\overset{R_1}{|}}{C}}-NH-CH_2-CH(OH)-Ar$$

wherein
$R_1$ is hydrogen or methyl,
$m$ is 0 or an integer from 1 to 8, inclusive, and
Ar is (a) [structure: phenyl ring with RO at top and $R_2$ at bottom-left]

where
R is hydrogen or acyl, and
$R_2$ is hydrogen or —OR, as defined above, (b) [structure: phenyl ring with $R_3$ at top and RO at bottom-left]

where
R has the meanings defined above, and
$R_3$ is hydroxy-lower alkyl, —NH—CO—$R_4$, —NH—SO₂—$R_5$, —CH₂—NH—CO—$R_4$, —CH₂—NH—SO₂—$R_5$ or —CH₂—NH—CO—NH—$R_4$,
where
$R_4$ is hydrogen or lower alkyl, and
$R_5$ is lower alkyl or di-lower alkyl-amino, (c) [structure: phenyl ring with $R_6$, X, Y substituents]

where
$R_6$ is hydrogen, amino or hydroxyl,
X is chlorine or bromine, and
Y is hydrogen, chlorine or bromine
or (d) [structure: bicyclic ring with RO and N-A]

where
R has the meanings defined above, and
A is a saturated or unsaturated 5- to 6-membered ring, and their non-toxic, pharmacologically acceptable acid addition salts; the compounds as well as their salts are useful as bronchospasmolytics, uterine spasmolytics, antipruritics and antiallergics.

7 Claims, No Drawings

N,N'-BIS-[(β-HYDROXY-β-PHENYL)-ETHYL]-POLYMETHYLENEDIAMINES AND SALTS THEREOF

This is a continuation of Ser. No. 246,711, filed Apr. 24, 1972, now abandoned.

This invention relates to novel N,N'-bis-[(β-hydroxy-β-phenyl)-ethyl]-polymethylenediamines and acid addition salts thereof, as well as to methods of preparing these compounds.

More particularly, the present invention relates to a novel class of N,N'-bis-[(β-hydroxy-β-phenyl)-ethyl]-polyethylenediamines of the formula

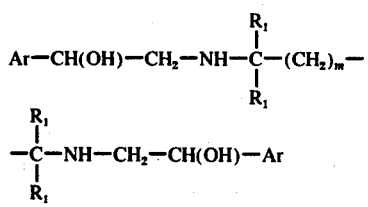

wherein
$R_1$ is hydrogen or methyl,
$m$ is 0 or an integer from 1 to 8, inclusive, and
Ar is (a) 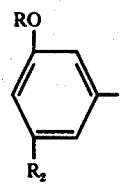 (II)

where
R is hydrogen or acyl, and
$R_2$ is hydrogen or -OR, as defined above, (b) 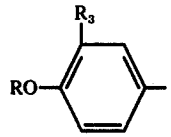 (III)

where
R has the meanings defined in formula II, and
$R_3$ is hydroxy-lower alkyl, —NH—CO— $R_4$, —NH—$SO_2$—$R_5$, —$CH_2$—NH—CO—$R_4$, —$CH_2$—NH—$SO_2$—$R_5$ or —$CH_2$—NH—CO— NH—$R_4$,
where
$R_4$ is hydrogen or lower alkyl, and
$R_5$ is lower alkyl or dilower alkyl-amino, (c) 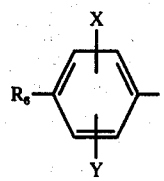 (IV)

where
$R_6$ is hydrogen, amino or hydroxyl,
X is chlorine or bromine, and
Y is hydrogen, chlorine or bromine, or (d) 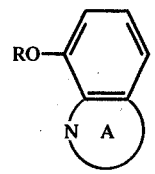 (V)

where
R has the meanings defined in formula II, and
A is a saturated or unsaturated 5-to 6-membered ring,
and their non-toxic, pharmacologically acceptable acid addition salts.

The compounds embraced by formula I may be prepared by the following conventional methods:

Method A

By reducing an aminoketone of the formula

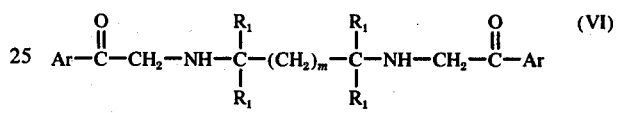 (VI)

wherein Ar and $R_1$ have the same meanings as in formula I, in accordance with conventional procedures.

For example, the reduction may be effected with the aid of a complex hydride, such as lithium aluminum hydride or sodium borohydride; or also with hydrogen in the presence of a hydrogenation catalyst, such as platinum, palladium or Raney nickel; or also by the Meerwein-Porndorf Reduction.

The starting compounds of the formula VI needed for this method may be obtained by reacting a compound of the formula

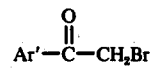 (VII)

wherein Ar' has the same meanings as Ar in formula I and, in addition, to the extent that Ar contains phenolic hydroxyl groups, these are free or protected by protective substituents which are removable by hydrolysis, alcoholysis or hydrogenation, with a polymethylenediamine of the formula

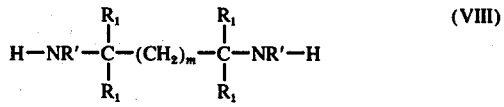 (VIII)

wherein $R_1$ and m have the same meanings as in formula I and R' is hydrogen or a substituent which is removable by hydrogenation, preferably unsubstituted or substituted benzyl, in the presence of a condensation agent, such as sodium carbonate, or an excess of the diamine of the formula VIII.

In those instances where the end product of the formula I is to contain acyl substituents, such as lower alkanoyl, these acyl substituents may already be present in the starting compound of the formula VII and may, of course, also function as protective substituents during the reaction with the diamine of the formula VIII.

For the preparation of a compound of the formula VI, the protective substituents in the reaction product of the condensation reaction between compound VII and compound VIII are, if necessary, removed therefrom by hydrolysis or hydrogenation pursuant to conventional methods.

Method B

By removing those substituents which are removable by hydrolysis, alcoholysis or hydrogenation from a compound of the formula

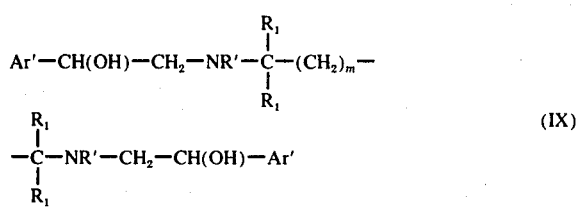

(IX)

wherein Ar' and R' have the meanings defined in formulas VII and VIII, respectively, by hydrolysis, alcoholysis or hydrogenation pursuant to conventional methods, depending upon what type of substituent is to be removed.

The starting compounds of the formula IX needed for this method may be prepared either by reducing an aminoketone of the formula

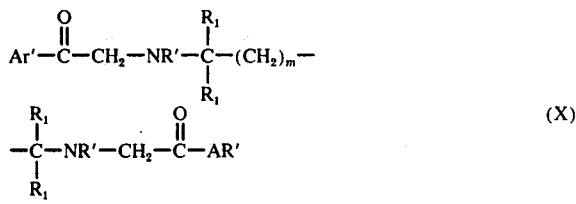

(X)

wherein $R_1$ and $m$ have the same meanings as in formula I and and Ar' and R' have the same meanings as in formula IX, in a manner analogous to that described in method A above, or by reacting an epoxide of the formula

(XI)

wherein Ar' has the meanings previously defined, with a polymethylenediamine of the formula VIII.

Of course, methods A and B described above may also be combined; that is, the reduction according to method A and the protective substituent removal according to method B may be carried out successively in a single reaction vessel by selectively choosing the proper reaction conditions for each step.

The compounds embraced by formula I are organic bases and occur in the form of racemic mixtures, optically inactive meso-isomers and optically active antipodes, and each of these isomeric forms combines with inorganic or organic acids to form acid addition salts. Examples of nontoxic, pharmacologically acceptable acid addition salts are those formed with hydrochloric acid, hydrobromic acid, sulfuric acid, acetic acid, propionic acid, maleic acid, methanesulfonic acid, 8-chlorotheophylline or the like.

The following examples further illustrate the present invention and will enable others skilled in the art to understand it more completely. It should be understood, however, that the invention is not limited solely to the particular examples given below.

EXAMPLE 1

N,N'-Bis-[β-hydroxy-β-(3',5'-dihydroxy-phenyl)-ethyl]-2,5-dimethyl-2,5-diamino-hexane and its dihydrochloride by method B.

2,5-Dimethyl-2,5-diamino-hexane was reacted with twice its molar equivalent of 3,5-dibenzyloxy-α-bromo-acetophenone (m.p. 83°–86° C) in acetonitrile in the presence of sodium carbonate, and the reaction product was subsequently reduced with sodium borohydride in ethanol. 5 gm of the N,N'-bis-[β-hydroxy-β-(3',5'-dibenzyloxy-phenyl)-ethyl]-2,5-dimethyl-2,5-diamino-hexane dihydrochloride (m.p. 180°–185° C) thus obtained were hydrogenated in 125 ml of methanol in the presence of Raney nickel as the catalyst at atmospheric pressure and room temperature. Thereafter, the catalyst was filtered off, and the methanol was distilled out of the filtrate. The residue, N,N'-bis-[β-hydroxy-β(3',-5'-dihyroxyphenyl)-ethyl]-2,5-dimethyl-2,5-diamino-hexane, was dissolved in a sufficient amount of ethanol, the resulting solution was acidified with ethereal hydrochloric acid, acetonitrile was added thereto, and the precipitate formed thereby was collected and recrystallized from 1 N hydrochloric acid, yielding the compound of the formula

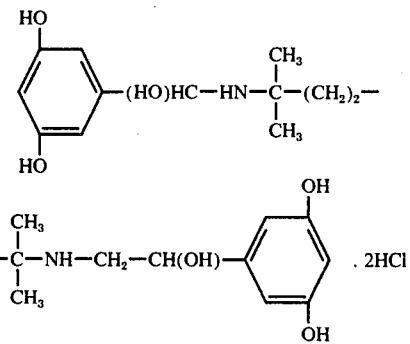

having a melting point of 275°–279° C.

EXAMPLE 2

N,N'-Bis-[β-hydroxy-β-(3'-hydroxymethyl-4'-hydroxy-phenyl)-ethyl]-2,5-dimethyl-2,5-diamino-hexane dihydrochloride by method B 2,5-Dimethyl-2,5-diamino-hexane was reacted with two molar equivalents of 4-benzyloxy-3-carbomethoxy-α-bromoacetophenone in acetonitrile to form N,N'-bis-[βoxo-β-(4'-benzyloxy-3'-carbomethoxy-phenyl)-ethyl]-2,5-dimethyl-2,5-diamino-hexane dihydrochloride (m.p. 133°–138° C), which was subsequently reduced with sodium borohydride in ethanol to form N,N'-bis-[β-hydroxy-β-(4'-benzyloxy-3'-carbomethoxyphenyl)-ethyl]2,5-dimethyl-2,5-diamino-hexane (m.p. 119°–122° C). 11 gm of this reduction product were dissolved in 50 ml of tetrahydrofuran, the resulting solution was added dropwise to a mixture of 500 ml of tetrahydrofuran and 7 gm of lithium aluminum hydride at 20° C while cooling the latter on an ice bath, and the resulting mixture was refluxed for three hours. Thereafter, the reaction solution was decomposed with water and vacuum-filtered, and the filtrate was evaporated, leaving N,N'-bis-[β-hydroxy-β-(4'-benzyloxy-3'-hydroxymethyl-phenyl)-ethyl]-2,5-dimethyl-2,5-diamino-hexane (m.p. 129°–132° C, from methanol).

The free base thus obtained was converted in isopropanol with ethereal hydrochloric acid into its dihydrochloride (m.p. 205°–208° C), and 4 gm of this salt were hydrogenated in a mixture of 100 ml of methanol and 10 ml of water in the presence of palladized charcoal as the catalyst at 1 atmosphere gauge and 20° C. Thereafter, the catalyst was filtered off, the solvent was evaporated out of the filtrate, and the crystalline precipitate formed thereby was collected and recrystallized from a mixture of water and acetonitrile, yielding the compound of the formula

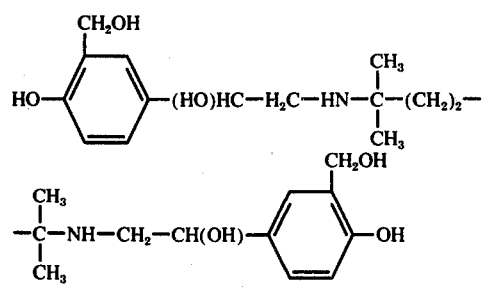

having a melting point higher than 350° C.

EXAMPLE 3

N,N'-Bis-[β-hydroxy-β-(3'-hydroxymethyl-4'-hydroxy-phenyl)-ethyl]-1,6-diamino-hexane and its sulfate.

N,N'-Dibenzyl-1,6-diamino-hexane was reacted with two molar equivalents of 4-benzyloxy-3-carbomethoxy-α-bromoacetophenone to form N,N'-bis-[β-oxo-β-(4'-benzyloxy-3'-carbomethoxy-phenyl)-ethyl]-N,N'-dibenzyl-1,6-diamino-hexane (m.p. of the dihydrochloride 108° C; from acetonitrile), which was subsequently reduced with lithium aluminum hydride, as described in Example 2, to form N,N'-bis-[β-hydroxy-β-(4'-benzyloxy-3'-hydroxymethyl-phenyl)-ethyl]-N,N'-dibenzyl-1,6-diamino-hexane. 37 gm of the base thus obtained were hydrogenated in 600 ml of methanol at 5 atmospheres gauge and 50° C in the presence of palladized charcoal as the catalyst, and after filtering off the catalyst the methanolic solution, which contained N,N'-bis-[β-hydroxy-β-(4'-hydroxy-3'-hydroxymethyl-phenyl)-ethyl]-1,6-diamino-hexane, was adjusted to pH 5.5 with concentrated sulfuric acid, while cooling on an ice bath and stirring. The crystalline precipitate formed thereby was collected and recrystallized from water, yielding the salt of the formula

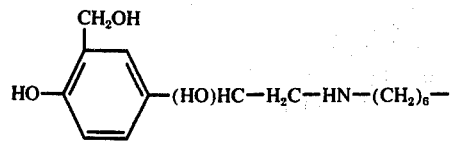
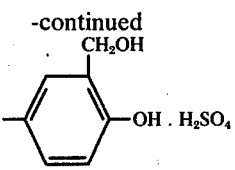

having a melting point higher than 350° C.

EXAMPLE 4

N,N'-Bis-[β-hydroxy-β-(2'-chloro-phenyl)-ethyl]-2,5-dimethyl-2,5-diamino-hexane, its maleate and its dihydrochloride A mixture consisting of 65 gm of 2-chloro-α-bromoacetophenone (b.p. 110° C at 1.5 mm Hg), 20 gm of 2,5-dimethyl-2,5-diamino-hexane, 40 gm of sodium carbonate and 500 ml of acetonitrile was refluxed for four hours. Thereafter, the reaction mixture was vacuum-filtered, and the filtrate was admixed with a solution of maleic acid in acetonitrile, whereupon N,N'-bis-[β-oxo-β-(2'-chloro-phenyl)-ethyl]-2,5-dimethyl-2,5-diamino-hexane maleate (m.p. 175°–178° C, from water) crystallized out. The free base liberated from 10 gm of the maleate by treatment with ammonia and extraction with ethyl acetate was admixed with 100 ml of ethanol and 1.0 gm of sodium borohydride, and the mixture was allowed to stand at room temperature for 12 hours. Thereafter, the reaction solution was evaporated, the residue was decomposed with hydrochloric acid, the acidic mixture was made alkaline with ammonia, and the resulting solution was extracted with ethyl acetate. The organic extract was evaporated, the residue was taken up in acetone, and the resulting solution was admixed with maleic acid, yielding N,N'-bis-[β-hydroxy-β-(2'-chloro-phenyl)-ethyl]-2,5-dimethyl-2,5-diamino-hexane maleate. The free base was liberated from the maleate by treatment with ammonia, dissolved in ethyl acetate, and the resulting solution was acidified with ethereal hydrochloric acid, yielding the dihydrochloride of the formula

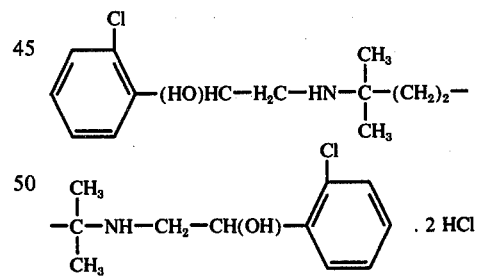

which had a melting point of 247°–249° C after recrystallization from glacial acetic acid.

EXAMPLE 5

N,N'-Bis-[β-hydroxy-β-(4'-hydroxy-3'-methylsulfonamidophenyl)-ethyl]-1,4-diamino-butane dihydrochloride N,N'-Dibenzyl-1,4-diamino-butane was reacted in acetone with two molar equivalents of 4-benzyloxy-3-methylsulfonamido-α-bromo-acetophenone (m.p. 115°–117° C) to form N,N'-bis-[β-oxo-β-(4'-benzyloxy-3'-methylsulfonamido-phenyl)-ethyl]-N,N'-dibenzyl-1,4-diamino-butane, which was converted into its dihydrochloride. The latter was hydrogenated in methanol in the presence of palladized charcoal at 5 atmospheres gauge and 60° C until the calculated amount of hydrogen had been absorbed, yielding N,N'-bis-[β-oxo-(4'-hydroxy-3'-methylsulfonamido-phenyl)-ethyl]-1,4-diamino-butane dihydrochloride (m.p. 258°–260° C, from water). 7 gm of this salt were hydrogenated in 200 ml of water in the presence of palladized charcoal as the catalyst at 5 atmospheres gauge and 60° C, the catalyst was separated by vacuum filtration, and the water was evaporated from the filtrate, leaving the dihydrochloride monohydrate of the formula

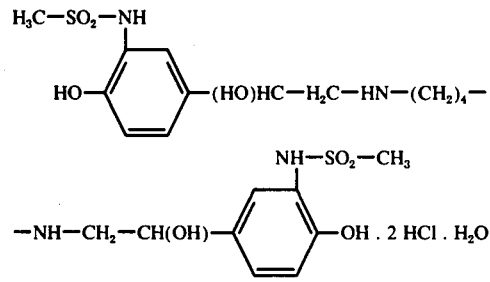

having a melting point of 226°–227° C (from water/ethanol).

EXAMPLE 6

N,N'-Bis-[β-hydroxy-β-(3'-hydroxy-phenyl)-ethyl]-2,5-dimethyl-2,5-diamino-hexane dihydrochloride A mixture consisting of 34 gm of 3-benzyloxy-α-bromo-acetophenone, 18 gm of N,N'-dibenzyl-2,5-dimethyl-2,5-diamino-hexane (b.p. 167°–168° C at 0.05 mm Hg), 15 gm of sodium carbonate and 125 ml of acetonitrile was refluxed for four hours. Thereafter, the reaction mixture was vacuum-filtered, and the filtrate was evaporated, leaving N,N'-bis-[β-oxo-β-(3'-benzyloxy-phenyl)-ethyl]-N,N'-dibenzyl-2,5-dimethyl-2,5-diamino-hexane. This compound was dissolved in 250 ml of methanol, the solution was acidified with ethereal hydrochloric acid, and the acid solution was hydrogenated in the presence of palladized charcoal as the catalyst at 60° C and 5 atmospheres gauge. Subsequently, the catalyst was filtered off, the solvent was evaporated from the filtrate, and the crystalline precipitate formed thereby was collected and recrystallized from a small amount of water, yielding the dihydrochloride of the formula

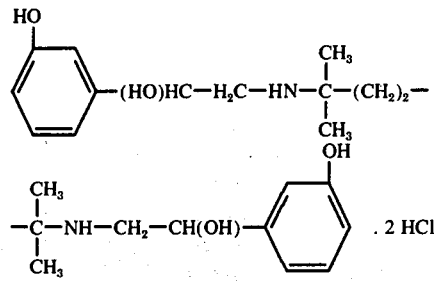

which had a melting point of 270°–273° C.

EXAMPLE 7

N,N'-Bis-[β-hydroxy-β-(3',5'-dihydroxy-phenyl)-ethyl]-1,6-diamino-hexane, its dihydrochloride and its sulfate N,N'-Dibenzyl-1,6-diamine-hexane was reacted in acetonitrile with two molar equivalents of 3,5-dibenzyloxy-α-bromo-acetophenone to form N,N'-bis-[β-oxo-β-(3',5'-dibenzyloxy-phenyl)-ethyl]-N,N'-dibenzyl-1,6-diamino-hexane, which was converted into its dihydrochloride (m.p. 158°–161° C). This salt was hydrogenated in a mixture of methanol and water (5:1) in the presence of palladized charcoal as the catalyst at 60° C and 5 atmospheres gauge to form N,N'-bis-[β-oxo-β-(3',5'-dihydroxy-phenyl)-ethyl]-1,6-diamino-hexane dihydrochloride (m.p. 306°–310° C, decomp.). 8 gm of this salt were hydrogenated in 200 ml of water at 50° C and 5 atmospheres gauge in the presence of palladized charcoal as the catalyst. Thereafter, the catalyst was separated by vacuum filtration, and the filtrate was evaporated, leaving the free base N,N'-bis-[-β-hydroxy-β-(3',5'-dihydroxy-phenyl)-ethyl]-1,6-diamino-hexane, which was admixed with a small amount of concentrated hydrochloric acid, causing the dihydrochloride to crystallize out. This salt was dissolved in a sufficient amount of warm water, and the resulting solution was admixed with a hot concentrated aqueous sodium sulfate solution. Upon cooling, a crystalline substance separated out which was collected and recrystallized from a small amount of water, yielding the sulfate of the formula

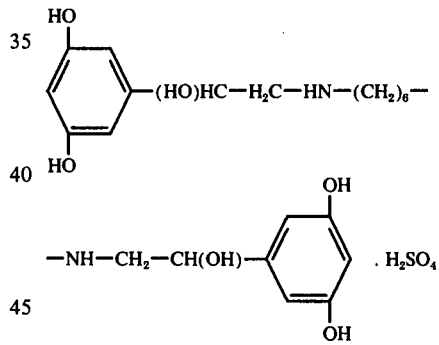

which had a melting point of 283° C (decomp.).

EXAMPLE 8

N,N'-Bis-[β-hydroxy-β-(3',5'-dichloro-4'-hydroxy-phenyl)-ethyl]-1,6-diamino-hexane and its dihydrochloride N,N'-Dibenzyl-1,6-diamino-hexane was reacted with two molar equivalents of 3,5-dichloro-4-hydroxy-α-bromo-acetophenone in acetonitrile in the presence of sodium carbonate to form N,N'-bis-[β-oxo-β-(3',5'-dichloro-4'-hydroxy-phenyl)-ethyl]-N,N'-dibenzyl-1,6-diamino-hexane, which was converted into its dihydrochloride. This salt was hydrogenated in methanol at 5 atmospheres gauge and 60° C in the presence of palladized charcoal, yielding N,N'-bis-[β-oxo-β-(3',5'-dichloro-4'-hydroxy-phenyl)-ethyl]-1,6-diamino-hexane dihydrochloride, m.p. 280° C (decomp.; from methanol/acetonitrile). 1.56 gm of this salt were reduced in 100 ml of ethanol and 10.5 ml of 1 N sodium hydroxide with 0.865 gm of sodium borohydride for twelve hours at room temperature, yielding the free base N,N'-bis-[β-hydroxy-β-(3',5'-dichloro-4'-hydroxy-phenyl)-ethyl]-1,6-diamino-hexane. The base was dissolved in acetonitrile, and the solution was acidified with ethereal hydrochloric acid, yielding the dihydrochloride of the formula

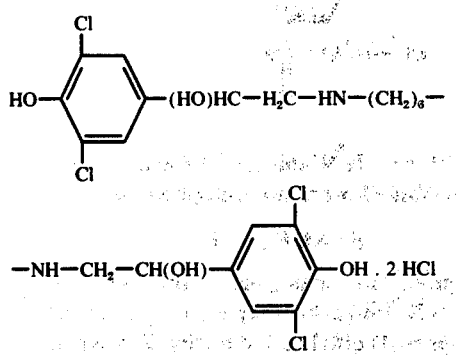

which had a melting point of 208°–209° C (decomp.).

EXAMPLE 9

N,N'-Bis-[β-hydroxy-β-(3'methylsulfonamido-4'-hydroxy-phenyl)-ethyl]-1,6-diamino-hexane dihydrochloride N,N'-Dibenzyl-1,6-diamino-hexane was reacted with two molar equivalents of 4-benzyloxy-3-methylsulfonamido-α-bromo-acetophenone in acetonitrile in the presence of sodium carbonate to form N,N'-bis-[β-oxo-β-(3'-methylsulfonamido-4'-benzyloxy-phenyl)-ethyl]-N,N'-dibenzyl-1,6-diamino-hexane, which was converted into its dihydrochloride. This salt was then hydrogenated in methanol at 60° C and 5 atmospheres gauge in the presence of palladized charcoal until the calculated amount of hydrogen had been adsorbed, yielding N,N'-bis-[β-oxo-β-(3'-methylsulfonamido-4'-hydroxy-phenyl)-ethyl]-1,6-diamino-hexane dihydrochloride, m.p. 250° C (decomp.; from water). 6 gm of this salt were hydrogenated in 100 ml of water at 5 atmospheres gauge and 60° C in the presence of palladized charcoal as the catalyst, the reaction mixture was vacuum-filtered, the filtrate was evaporated, and the residue was recrystallized from water/ethanol, yielding the dihydrochloride of the formula

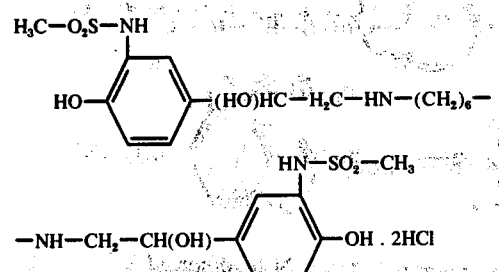

which had a melting point of 211°–213° C (decomp.).

EXAMPLE 10

N,N'-Bis-[β-hydroxy-β-(3',5'-dihyroxy-phenyl)-ethyl]-2,7-dimethyl-2,7-diamino-octane and its sulfate N,N'-Dibenzyl-2,7-dimethyl-2,7-diamino-octane was reacted with two molar equivalents of 3,5-dibenzyloxy-α-bromo-acetophenone in acetonitrile in the presence of sodium carbonate to form N,N'-bis-[β-oxo-β-(3',5'-dibenzyloxy-phenyl)-ethyl]-2,7-dimethyl-2,7-diamino-octane (m.p. of its dihydrochloride 170°–172° C), which was then reduced with sodium borohydride to yield N,N'-bis-[β-hydroxy-β-(3',5'-dibenzyloxy-phenyl)-ethyl]-N,N'-dibenzyl-2,7-dimethyl-2,7-diamino-octane, m.p. 108°–110° C. The free base thus obtained was hydrogenated in glacial acetic acid at 50° C and 5 atmospheres gauge in the presence of palladized charcoal, the reaction mixture was vacuum-filtered, the filtrate was evaporated, and the crystalline residue was recrystallized from ethanol, yielding the free base N,N'-bis-[β-hydroxy-β-(3',5'-dihydroxy-phenyl)-ethyl]-2,7-dimethyl-2,7-diamino-octane. The base was dissolved in hot water, the solution was admixed with a saturated aqueous solution of sodium sulfate, the mixture was allowed to cool, and the crystalline precipitate formed thereby was collected and recrystallized from water, yielding the sulfate of the formula

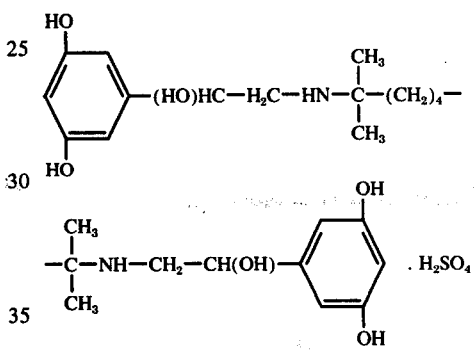

which had a melting point of 245° C.

EXAMPLE 11

N,N'-Bis-[β-hydroxy-β-(3'-dimethylaminosulfonamido-phenyl)-ethyl]-1,8-diamino-octane dihydrochloride N,N'-Dibenzyl-1,8-diamino-octane was reacted with two molar equivalents of 4-benzyloxy-3-dimethylaminosulfonamido-α-bromo-acetophenone in acetonitrile in the presence of sodium carbonate to form N,N'-bis-[β-oxo-β-(3'-dimethylaminosulfonamido-4'-benzyloxy-phenyl)-ethyl]-N,N'-dibenzyl-1,8-diamino-octane, which was converted into its dihydrochloride. This salt was then hydrogenated in methanol at 60° C and 5 atmospheres gauge in the presence of palladized charcoal until the calculated amount of hydrogen had been absorbed, yielding N,N'-bis-[β-oxo-β-(3'-dimethylaminosulfonamido-4'-hydroxy-phenyl)-ethyl]-1,8-diamino-octane dihydrochloride, m.p. 184° C (decomp.; from 1 N hydrochloric acid). 3.5 gm of this salt were hydrogenated in methanol at atmospheric pressure and room temperature in the presence of platinum as the catalyst, the reaction mixture was filtered, the filtrate was evaporated, the residue was triturated with glacial acetic acid, and the crystalline substance formed thereby was collected and recrystallized from 1 N hydrochloric acid, yielding the dihydrochloride of the formula

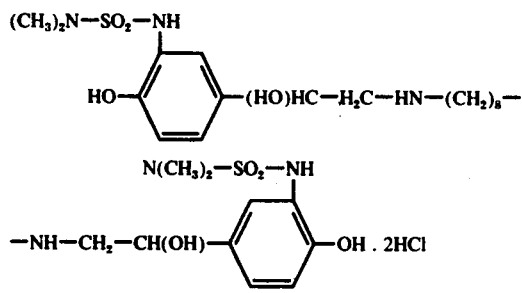

which had a melting point of 185°–186° C (decomp.).

EXAMPLE 12

Using a procedure analogous to that described in Example 7, N,N'-bis-[β-hydroxy-β-(3',5'-diacetoxyphenyl)-ethyl]-1,6-diamino-hexane dihydrochloride of the formula

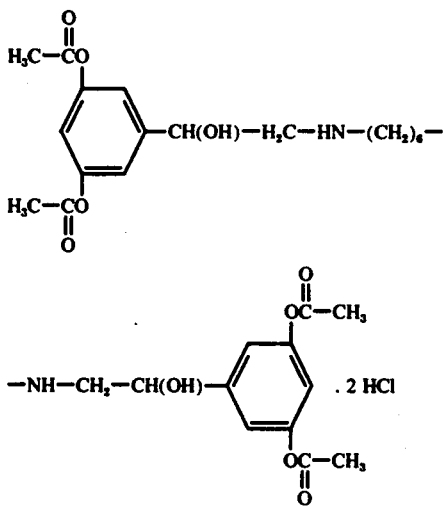

was prepared from N,N'-dibenzyl-1,6-diamino-hexane and 3,5-diacetoxy-α-bromo-acetophenone.

EXAMPLE 13

Using a procedure analogous to that described in Example 7, N,N'-bis-[β-hydroxy-β-(3',5'-diheptanoyloxy-phenyl)-ethyl]-1,6-diamino-hexane dihydrochloride of the formula

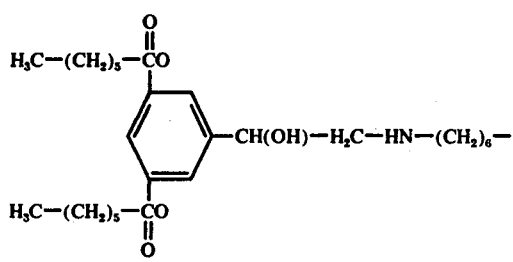

was prepared from N,N'-dibenzyl-1,6-diamino-hexane and 3,5-diheptanoyl-α-bromo-acetophenone.

EXAMPLE 14

Using a procedure analogous to that described in Example 3, N,N'-bis-[β-hydroxy-β-(3'-hydroxymethyl-4'-hydroxy-phenyl)-ethyl]-2,7-dimethyl-2,7-diamino-octane sulfate of the formula

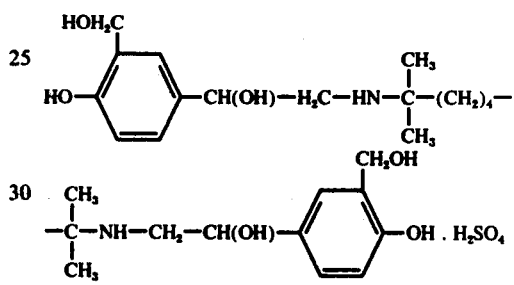

was prepared from N,N'-dibenzyl-2,7-dimethyl-2,7-diamino-octane and 4-benzyloxy-3-carbomethoxy-α-bromo-acetophenone.

EXAMPLE 15

Using a procedure analogous to that described in Example 5, N,N'-bis-[β-hydroxy-β-(3'-methylsulfonamido-4'-hydroxy-phenyl)-ethyl]-2,7-dimethyl-2,7-diamino-octane dihydrochloride of the formula

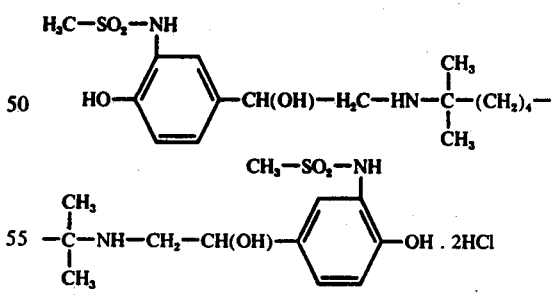

was prepared from N,N'-dibenzyl-2,7-dimethyl-2,7-diamino-octane and 4-benzyloxy-3-methylsulfonamido-α-bromo-acetophenone.

EXAMPLE 16

Using a procedure analogous to that described in Example 4, N,N'-bis-[β-hydroxy-β-(2'-chloro-4'-hydroxy-phenyl)-ethyl]-1,6-diamino-hexane dihydrochloride of the formula

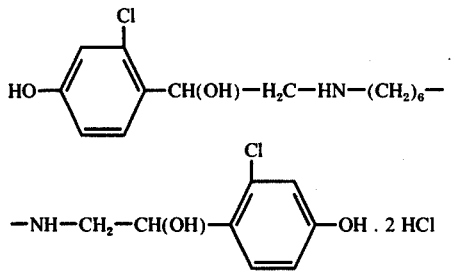

was prepared from 1,6-diamino-hexane and 2-chloro-4-benzyloxy-α-bromo-acetophenone.

EXAMPLE 17

Using a procedure analogous to that described in Example 8, N,N'-bis-[β-hydroxy-β-(3',5'-dichloro-4'-aminophenyl)-ethyl]-2,5-dimethyl-2,5-diamino-hexane sulfate of the formula

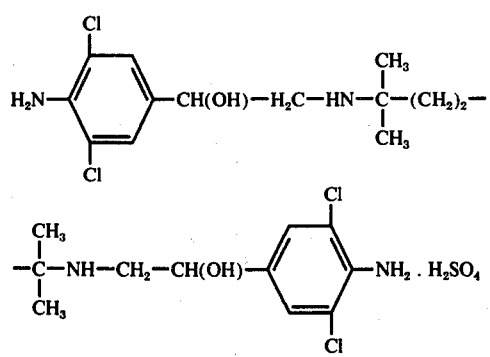

was prepared from N,N'-dibenzyl-2,5-dimethyl-2,5-diamino-hexane and 3,5-dichloro-4-amino-α-bromo-acetophenone.

EXAMPLE 18

Using a procedure analogous to that described in Example 3, N,N'-bis-[β-hydroxy-β-(3'-β'-hydroxyethyl-4'-hydroxy-phenyl)-ethyl]-1,6-diamino-hexane dihydrochloride of the formula

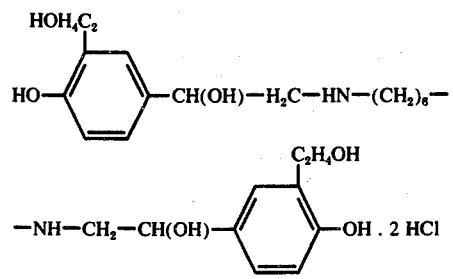

was prepared from N,N'-dibenzyl-1,6-diamino-hexane and 4-benzyloxy-3-carbethoxy-α-bromo-acetophenone.

EXAMPLE 19

Using a procedure analogous to that described in Example 5, N,N'-bis-[β-hydroxy-β-(3'-methylsulfonamidomethyl-4'-hydroxy-phenyl)-ethyl]-1,6-diamino-hexane dihydrochloride of the formula

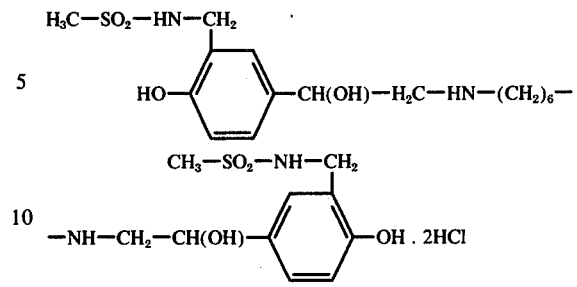

was prepared from N,N'-dibenzyl-1,6-diamino-hexane and 4-benzyloxy-3-methylsulfonamidomethyl-α-bromo-acetophenone.

EXAMPLE 20

Using a procedure analogous to that described in Example 5, N,N'-bis-[β-hydroxy-β-(3'-ureidomethyl-4'-hydroxy-phenyl)-ethyl]-1,6-diamino-hexane dihydrochloride of the formula

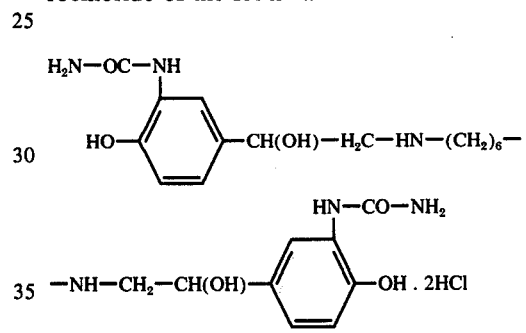

was prepared from N,N'-dibenzyl-1,6-diamino-hexane and 3-ureido-4-benzyloxy-α-bromo-acetophenone.

EXAMPLE 21

Using a procedure analogous to that described in Example 5, N,N'-bis-[β-hydroxy-β-(3'-acetamido-4'-hydroxy-phenyl)-ethyl]-1,6-diamino-hexane dihydrochloride of the formula

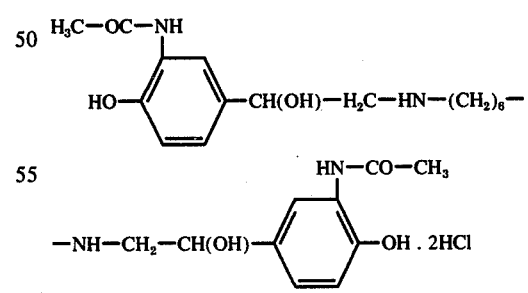

was prepared from N,N'-dibenzyl-1,6-diamino-hexane and 3-acetamido-4-benzyloxy-α-bromo-acetophenone.

EXAMPLE 22

Using a procedure analogous to that described in Example 5, N,N'-bis-[β-hydroxy-β-(3'-formamido-4'-hydroxy-phenyl)-ethyl]-1,6-diamino-hexane dihydrochloride of the formula

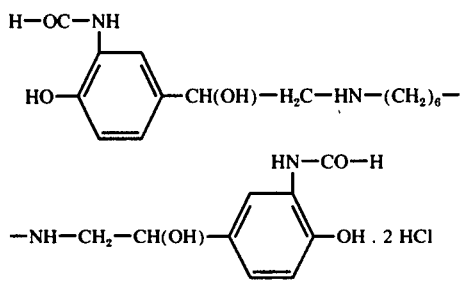

was prepared from N,N'-dibenzyl-1,6-diamino-hexane and 3-formamido-4-benzyloxy-α-bromo-acetophenone.

The compounds according to the present invention, that is, those embraced by formula I above and their non-toxic acid addition salts, have useful pharmacodynamic properties. More particularly, the compounds of the instant invention exhibit bronchospasmolytic, uterine spasmolytic, anti-pruritic and antiallergic activities in warm-blooded animals, such as mice, rats, dogs, cats and minks.

With respect to their bronchospasmolytic activity, the compounds of the present invention are superior to known polymethylenediamines of related structure in that the former are characterized by a more advantageous ratio between the desirable bronchospasmolytic activity and undesirable side-effects, especially cardiac effects.

Particularly effective among the compounds of the invention are those of the formula I wherein m is an integer from 2 to 6, inclusive,
$R_1$ is hydrogen or methyl, and
Ar is

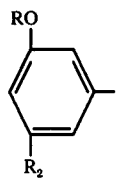

where
R is hydrogen or alkanoyl of 2 to 7 carbon atoms, and
$R_2$ is —OR, as defined above,

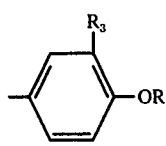

where
R has the meanings defined above, and
$R_3$ is —CH₂OH, —Ch₂—CH₂OH, —NH—SO₂—CH₃, —NH—CO—H, —NH—CO—CH₃, —CH₂—NH—CO—NH₂ or —CH₂—NH—SO₂—CH₃,
or

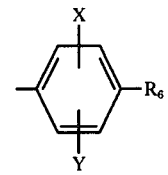

where
$R_6$ is hydroxyl or amino,
X is chlorine, and
Y is hydrogen or chlorine,
and their non-toxic, pharmacologically acceptable acid addition salts.

Especially effective are those compounds of the formula I wherein m is 2 or 4,
$R_1$ is hydrogen or methyl, and
Ar is 3,5-dihydroxy-phenyl, 3-hydroxymethyl-4-hydroxy-phenyl, 3-methylsulfonamido-4-hydroxy-phenyl, 2-chloro-4-hydroxy-phenyl or 3,5-dichloro-4-amino-phenyl, and their non-toxic, pharmacologically acceptable acid addition salts.

For pharmaceutical purposes the compounds according to the present invention are administered to warm-blooded animals topically, perorally or per inhalationem (by the respiratory route) as active ingredients in customary pharmaceutical compositions, that is, compositions consisting essentially of an inert pharmaceutical carrier and an effective amount of the active ingredient, such as tablets, coated pills, capsules, solutions, ointments, tinctures, aerosol sprays and the like.

One effective peroral dosage unit of the compounds of the invention is from 0.083 to 0.83 mgm/kg body weight.

Their effective concentration in compositions for topical administration is from 0.1 to 5 % by weight, based on the total weight of the composition.

For administration by the respiratory route the effective concentration is from 0.1 to 5 % by weight, based on the total weight of the spray composition.

The following examples illustrate a few pharmaceutical compositions comprising a compound of the present invention as an active ingredient and represent the best mode contemplated of putting the invention into practical use. The parts are parts by weight unless otherwise specified.

EXAMPLE 23

Tablets

The tablet composition is compounded from the following ingredients:

| | |
|---|---|
| N,N'-Bis-[β-hydroxy-β-(3'-hydroxymethyl-4'-hydroxy-phenyl)-ethyl]-2,5-dimethyl-2,5-diamino-hexane · 2 HCl | 20 parts |
| Stearic acid | 6 parts |
| Dextrose | 574 parts |
| Total | 600 parts |

The ingredients are admixed and the mixture is compressed into 600 mgm-tablets in conventional manner. Each tablet contains 20 mgm of the diaminohexane salt and is an oral dosage unit composition with effective bronchospasmolytic, antipruritic and antiallergic action.

EXAMPLE 24

Ointment

The ointment composition is compounded from the following ingredients:

| | |
|---|---|
| N,N'-Bis-[β-hydroxy-β-(3',5'-dihydroxy-phenyl)-ethyl]-2,5-dimethyl-2,5-diamino-hexane · 2 HCl | 0.200 parts |
| Fuming hydrochloric acid | 0.011 parts |
| Sodium pyrosulfite | 0.050 parts |
| Mixture of equal parts of cetyl alcohol and stearyl alcohol | 18.000 parts |
| White vaseline | 5.000 parts |
| Synthetic bergamot oil | 0.075 parts |
| Distilled water q.s.ad | 100.000 parts |

The ingredients are compounded in conventional manner into an ointment which is a topical pharmaceutical composition with effective antipruritic and antiallergic actions.

EXAMPLE 25

Inhalation Aerosol

The aerosol composition is compounded from the following ingredients:

| | |
|---|---|
| N,N'-Bis-[β-hydroxy-β-(3'-methylsulfon-amido-4'-hydroxy-phenyl)-ethyl]-1,4-diamino-butane · 2HCl | 0.20 parts |
| Soybean lecithin | 0.05 parts |
| Propellant gas mixture (Frigen 11, 12 and 114 q.s.ad | 100.00 parts |

The ingredients are compounded and filled in conventional manner into aerosol containers provided with a metering valve which releases from 0.05 to 2.0 mgm of the diamino-butane compound with each actuation. The aerosol is a dosage unit composition for administration by the respiratory route with effective bronchospasmolytic action.

Analogous results are obtained when any one of the other polymethylenediamines embraced by formula I or a non-toxic acid addition salt thereof is substituted for the particular polymethylenediamine in Examples 23 through 25. Likewise, the amount of active ingredient in these illustrative examples may be varied to achieve the dosage unit or concentration range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

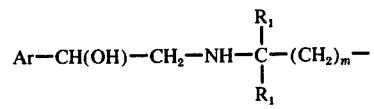

-continued

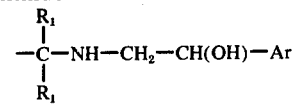

wherein
$R_1$ is hydrogen or methyl,
$m$ is 0 or an integer from 1 to 8, inclusive, and
Ar is

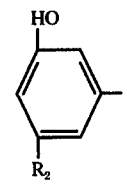  (a)

where $R_2$ is hydrogen or hydroxyl,

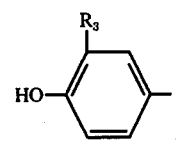  (b)

where $R_3$ is hydroxy-lower alkyl, or

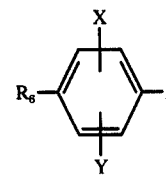  (c)

where
$R_6$ is hydrogen, amino or hydroxyl,
X is chlorine or bromine, and
Y is hydrogen, chlorine or bromine
or a non-toxic, pharmacologically acceptable acid addition salt thereof.

2. A compound of claim 1, wherein
$R_1$ is hydrogen or methyl,
$m$ is an integer from 2 to 6, inclusive and
Ar is (a) 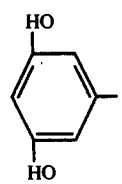

(b) 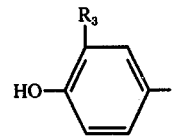

where $R_3$ is hydroxy-methyl or hydroxy-ethyl, or (c) 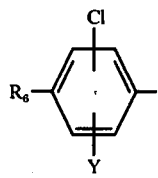

where $R_6$ is hydroxyl or amino, and

Y is hydrogen or chlorine, or a non-toxic, pharmacologically acceptable acid addition salt thereof.

3. A compound of claim 1, wherein $R_1$ is hydrogen or methyl, m is 2 or 4, and

Ar is 3,5-dihydroxy-phenyl, 3-hydroxymethyl-4-hydroxy-phenyl, 2-chloro-4-hydroxy-phenyl or 3,5-dichloro-4-amino-phenyl, or a non-toxic, pharmacologically acceptable acid addition salt thereof.

4. A compound of claim 3, which is N,N'-bis-[β-hydroxy-β-(3', 5'-dihydroxy-phenyl)-ethyl]-2,5-dimethyl-2,5-diamino-hexane or a non-toxic, pharmacologically acceptable acid addition salt thereof.

5. A compound of claim 3, which is N,N'-bis-[β-hydroxy-β-(3'-hydroxymethyl-4'-hydroxy-phenyl)-ethyl]-2,5-dimethyl-2,5-diamino-hexane or a non-toxic, pharmacologically acceptable acid addition salt thereof.

6. A compound of claim 3, which is N,N'-bis-[β-hydroxy-β-(3'-hydroxymethyl-4'-hydroxy-phenyl)-ethyl]-1,6-diamino-hexane or a non-toxic, pharmacologically acceptable acid addition salt thereof.

7. A compound of claim 3, which is N,N'-bis-[β-hydroxy-β-(3',5'-dihydroxy-phenyl)-ethyl]-1,6-diamino-hexane or a non-toxic, pharmacologically acceptable acid addition salt thereof.

* * * * *